United States Patent [19]

Nambu

[11] Patent Number: 4,617,271
[45] Date of Patent: Oct. 14, 1986

[54] PROCESS FOR PRODUCING IMMOBILIZED L-ASPARAGINASE PREPARATIONS FOR THE THERAPY OF LEUKEMIA

[75] Inventor: Masao Nambu, Yokohama, Japan

[73] Assignee: Nippon Oil Company, Limited, Tokyo, Japan

[21] Appl. No.: 573,922

[22] PCT Filed: Apr. 21, 1983

[86] PCT No.: PCT/JP83/00126
§ 371 Date: Dec. 16, 1983
§ 102(e) Date: Dec. 16, 1983

[87] PCT Pub. No.: WO83/03763
PCT Pub. Date: Nov. 10, 1983

[30] Foreign Application Priority Data

Apr. 21, 1982 [JP] Japan .................. 57-65466

[51] Int. Cl.$^4$ ...................... C12N 11/04; C12N 11/02; C12N 11/08; C12N 9/82
[52] U.S. Cl. ..................................... 435/182; 435/177; 435/180; 435/229
[58] Field of Search ................ 435/180, 182, 177, 229

[56] References Cited

U.S. PATENT DOCUMENTS 3,859,169  1/1975  O'Driscoll et al. ................. 435/182

FOREIGN PATENT DOCUMENTS 52276  5/1975  Japan .
52-008071  1/1977  Japan ..................................... 264/28

Primary Examiner—Sidney Marantz
Assistant Examiner—L. Krawczewicz
Attorney, Agent, or Firm—Scully, Scott, Murphy & Presser

[57] ABSTRACT

This invention relates to a process for producing immobilized L-asparaginase preparations. Its principal object is to produce immobilized L-asparaginase preparations which are excellent in antithrombogenicity and mechanical strength.

The present invention is concerned with production of immobilized L-asparaginase preparations by pouring an aqueous solution containing 6% or more of a polyvinyl alcohol with a degree of hydrolysis of 97 mol. % or higher and a viscosity-average degree of polymerization of 1,800 or more an antileukemic asparaginase into a vessel or a mold of an appropriate shape, subjecting the solution to cooling, solidification and molding at a temperature of $-15°$ C. or lower and partially dehydrating the molded mass without thawing to a dehydration ratio of 5% by weight or more and, if desired, immersing the product in water.

According to the invention, L-asparaginase can be embedded in a highly hydrous gel excellent in antithrombogenicity and mechanical strength by simple procedures.

7 Claims, No Drawings

PROCESS FOR PRODUCING IMMOBILIZED L-ASPARAGINASE PREPARATIONS FOR THE THERAPY OF LEUKEMIA

FIELD OF THE INVENTION

This invention relates to a process for producing immobilized L-asparaginase preparations for the therapy of leukemia. Particularly, it is concerned with a process for preparing enzymatical leukemia-curing agents by embedding (immobilizing) asparaginase, an antileukemic enzyme (L-asparaginase) in a highly hydrous gel excellent in antithrombogenicity and mechanical strength.

BACKGROUND OF THE INVENTION

It has long been pointed out that asparagine is essential (an essential amino acid) for the growth of leukemic cells. Extensive studies have been on the therapy of leukemia by eliminating asparagine which is not necessarily essential (non-essential) for normal cells from blood, which therapy is expected to cause no damage to normal cells (L. T. Mashburn et al., Biochem. Biophys. Res. Commun., 12, 50 (1963)). Whereas normal cells in which asparagine is formed from aspartic acid or aspartates with asparagine synthetase, an asparagine-synthesizing enzyme, leukemic cells which is deficient in the asparagine-synthesizing activity due to tumorigenesis and in which no asparagine is formed make use of the asparagine existing in plasma in a very small amount for the protein synthesis. Therefore, the therapy is based upon the idea that the protein synthesis (growth) of leukemic cells will be inhibited by introducing asparaginase into blood of the patient in order to decompose the asparagine in blood (achieve and maintain asparagine deficiency).

It is demonstrated that a variety of asparaginases are useful for the therapy of certain leukemias and solid tumors including acute lymphatic leukemia. This therapy was called attention as a specific and favorable therapeutic idea which represents inhibition (prevention) of the growth of leukemic cells without damaging normal cells (H. Marquardt, Arzneimittel-Forsch., 18, 1380 (1968)). Clinical trials were extensively carried out using asparaginase from *Escherichia coli* B (R. H. Adamson et al., Cancer Chemother. Rep., (1) 52, 617 (1968)). It was pointed out as a result of the trials that antigen-antibody reaction (immunoreaction) due to administration of a foreign protein in the human body was a problem; side effects such as vomiting, nausea, anorexia, pyrexia, bodyweight decrease, hypohepatia, pancreatitis, oligochromemia, uremia, fibrinogenopenia, hyponoia, skin rash, diarrhea, pararitium, anemia, leukopenia, thrombocytopenia, anaphylaxic shock, cephalalgia, angiodynia, irritation and cramp were observed (P. Laboureur, Pathol. Biol. (Paris), 17, 885 (1969)). Accordingly, the therapeutic method has been considered to be of little practical usefulness despite its causing little damage to normal cells, and, contrary to earlier expectation, there has been applied to some extent combination therapy with chemotherapeutic agents such as prednisone, vincristine, methotrexate, 6-mercaptopurine, cytarabine and cyclophosphamide, and radiotherapy. If there were provided means for avoiding the immunoreaction caused by the foreign protein, it is expected that the therapy will recover great hope. As a means of the solution there has been proposed a scheme in which blood is temporarily drawn out of the body, contacted with immobilized asparaginase (macromolecular material with the enzyme embedded or bound) to decompose the asparagine dissolved in the blood and then returned to the body (extracorporeal circulation) (D. Sampson et al., Trans. Am. Soc. Artif. Intern. Organs, 18, 54 (1972)). In this scheme, however, coagulation of the circulated blood by contact with the enzyme-immobilizing material (macromolecular material) is a newly caused problem, although the immunoreaction with the foreign protein (enzyme) is greatly weakened (or abolished) by employing an adequate enzyme-immobilization technique.

An expedient may be adopted to add an anti-coagulant such as heparin to the blood stream in consideration of poor antithrombogenicity in any of the known enzyme-immobilizing macromolecular materials. Combined use of drugs including heparin in a large amount for a long period of time itself is physiologically undesirable. Therefore, it has been desired to develop macromolecular materials which are capable of not only firmly immobilizing and maintaining asparaginase but also being free of immunoreaction with the enzyme as well as producing no thrombosis by contact with blood stream.

The present invention provides novel antithrombogenic macromolecular materials for immobilizing the enzyme which is suitable for the aforementioned needs.

Thrombosis or deposition of blood components upon the contact surface of a synthetic or natural macromolecular material with blood in medical use has long been recognized as an important problem to be overcome in developing artificial valve, blood vessel, kidney, catheter and the like. Efforts has been continued to find materials which hardly behave as foreign matter to blood, that is, materials which hardly cause thrombus due to destruction of the blood.

A number of attempts have been made to incorporate a minimum amount of an anticoagulant in the surface of a prosthesis based upon an idea that an anticoagulant may not be present throughout the body (circulating blood) in order to prevent coagulation on the contact surface of a prosthesis with blood. For example, application of an anticoagulant such as heparin, hirudin or antithrombin, a platelet-agglutination inhibitor such as adenylcyclase, prostaglandin E or methylxanthine, or a fibrinolysis activator such as urokinase or streptokinase on the surface of a prosthesis, the adsorption via ion-binding functional group, and the fixing on the surface of a prosthesis by means of covalent bond are known. However, the application or adsorption method is disadvantageous in that the anticoagulant and other agents are readily eliminated to have a short effective period of time. The covalent bond method also is not considered as useful, because there is often associated destruction of the anticoagulant by application of the chemical reaction and is possibility of producing adverse reactions to the body by the introduction of covalent functional group; it is also expected that effect of the anticoagulant fixed by means of a covalent bond is not sufficiently high (H. Tanzawa et al., Trans. Am. Soc. Artif. Intern. Organs, 19, 188 (1973)).

In order to avoid such difficulties blending and embedding of an anticoagulant in a prosthesis have been attempted (H. Tanzawa et al., Trans. Am. Soc. Artif. Intern. Organs, 19, 188 (1973)). It is however pointed out that the anticoagulant without fixing (entrapping) treatment by means of a chemical bond is apt to be eluted (released) entirely in a short period of time. The effective period of time is recognized to be 5-8 hours and at longest about 5 days. Therefore, needs for new superior antithrombogenic materials are high.

The present invention provides novel highly antithrombogenic medical materials comprising hydrogels with a high mechanical strength.

The invention provides a process for producing immobilized enzyme preparations by embedding asparaginase in a specific anticoagulant hydrogel.

The invention provides immobilized enzyme preparations in which the subject L-asparaginase is firmly embedded in a medical hydrogel without any damage so as to be sufficiently active because of absence of a conventional chemical bonding process using a chemical reagent or radiation.

In the present invention, polyvinyl alcohol is employed as the starting material for the preparation of an antithrombogenic hydrogel. There have been proposed many methods of the gel formation (preparation of hydrogels) of polyvinyl alcohol. However, as summarized below, all of the methods involve problems in operation or in properties of the product.

(1) By air-drying an aqueous polyvinyl alcohol solution there is obtained a wet or dry film, which, however, is merely a weak film being inferior in resistance to water and having no rigidity in water and is useful in limited applications only (Japanese Patent Publication No. 9523/1965).

(2) Also by adding an acid to an aqueous suspension containing polyvinyl alcohol and tetraethyl silicate, there is obtained a film similar to the one under (1) above only. In this method, addition of an acid to an aqueous solution followed lyophilization is also proposed. The resulting film, however, is of a lower strength and is scarcely moldable (Japanese Patent Publications Nos. 30358/1980 and 11311/1980).

(3) A gelation method involving irradiation of an aqueous polyvinyl alcohol solution with cobalt 60 ($\gamma$-ray) is well known. The method, however, not only requires special equipment (facilities for the irradiation) and is high in irradiation cost, but also produces only weak gels which often require an additional hardening process (secondary hardening). Therefore, the gel obtained by this method is of little use except for special applications such as for an artificial vitreous body (intra-eyeball filling liquid) for which a highly viscous liquid (or a soft gel) is desired (J. Material Sci., 1974, 1815 and Japanese Patent Laid Open No. 55647/1975).

(4) Also, it has long been known that an aqueous polyvinyl alcohol solution is gelled promptly upon mixing with boric acid (or an aqueous borax solution) (Note: borax=sodium tetraborate decahydrate). However, the resultant gel is weak and fluid; besides, it is torn immediately when picked up with finger tips so that it is difficult to retain its shape when molded (J. Am. Chem. Soc., 60, 1045 (1938) and French Patent No. 743942 (1933)).

Moreover, although the borax gel is existing in an alkaline condition, it is collapsed at a pH not higher than 8. Therefore, it is hardly usable and of little value for the medical application.

(5) There have also been proposed various gelation methods of polyvinyl alcohol by the use of phenols such as phenol, naphthol or Congo Red, an amino compound or a metallic compound such as a titanium, chromium or zirconium compound. In all of these methods, however, the same drawbacks as in the foregoing (4) are encountered (Japanese Patent Publications Nos. 9523/1965 and 23204/1965).

(6) It is also well known to gel a polyvinyl alcohol using a cross-linking agent or a copolymerization component such as an aldehyde, a dialdehyde, an unsaturated nitrile, a diisocyanate, trimethylolmelamine, epichlorohydrin, bis($\beta$-hydroxyethyl)sulfone, polyacrylic acid, dimethylolurea or maleic anhydride. This method, however, not only requires a process with a chemical reagent but also hardly produces a strong highly hydrous gel (Textile Res. J., (3) 189 (1962) and British Patent No. 742,900 (1958)).

(7) Also, it has long been known to gel an aqueous polyvinyl alcohol solution by allowing it to stand at a low temperature not higher than 40° C., particularly from 5° to 18° C. or lower.

However, the gels formed at room temperature are fragile like agar or carrageenan. Besides, they are dissolved merely by vigorously stirring, stirring after addition of water or slightly warming.

It is also known that it is preferable to employ a low temperature in order to prepare the cooled gel of an aqueous polyvinyl alcohol solution. For example, it is known to carry out the preparation at 18° C., at a low temperature not higher than 0° C. or at a lower temperature (Polymer J., 6, 103 (1974)).

In any case, however, the gel thus obtained is a weak gel (or viscous liquid) like agar, carrageenan or jelly. It is not only very sticky but also is poor in resistance to water so that it is swollen in water to a remarkable extent and further softened; it is partly dissolved out in water and becomes paste-like for the remainder. In water or in warm water at 40°-50° C., the gel is more rapidly deformed and dispersed or dissolved in water. These drawbacks make it hardly valuable for medical use.

(8) Sponge-like product obtained by formalization of polyvinyl alcohol also has long been known. As it is unstable in tissue, in which as it is decomposed or degenerated it produces adverse reactions in the circumstances, the use has recently been very restricted (J. R. Lewis, Plastic & Reconstructive Surgery, 35, 51 (1965)).

(9) It is also known to add a small amount of polyvinyl alcohol to an aqueous solution of a water-soluble macromolecular substance capable of being gelled such as agarose, agar, albumin, alginate, curdlan, carrageenan, casein, CMC, furcellaran, gelatin, methylcellulose, pectin, starch, tamarind gum, xanthan gum, tragacanth gum or guar gum and cool the mixture, immerse it in a gelling agent-containing bath (coagulation bath) or freeze-dry it (Japanese Patent Publications Nos. 25210/1981 and 25211/1981). Also by such method there is obtained only a weak viscous liquid poor in resistance to water, a non-fluid gel or a water-soluble dry powder only.

As a result of studies with an object of developing a process for producing water-insoluble antithrombogenic highly hydrous immobilized enzyme preparations with excellent mechanical properties by the use of polyvinyl alcohol, it was previously found by us that highly hydrous gels with enzyme embedded which had a water content of 45-92% by weight were produced by subjecting an aqueous solution containing polyvinyl alcohol and enzyme to cooling, solidifying and molding at a temperature lower than −15° C. under specified conditions and subsequently, without thawing, to partial dehydration under vacuum (U.S. patent application No.

344,006). The present invention represents further development of the above-mentioned finding. The hydrogels obtained according to the invention does not produce any damage in L-asparaginase, because, in the gelation process and its pretreatment, there is need of none of the acid, alkali, radical source, radiation, organic solvent, reagent and inorganic solvent other than water which are conventionally used in the prior-art gel formation or enzyme immobilization. Moreover, the gels obtained according to the invention are high in water content and are of both rubber-like elasticity and high mechanical strength. The gels of the invention are also insoluble in cold or warm water and non-sticky thereby being entirely differentiated from the aforementioned gels produced by cooling an aqueous solution of polyvinyl alcohol. Thus, the present invention provide a process for preparing L-asparaginase-immobilizing agents by the use of a novel antithrombogenic gel which is entirely different from the prior finding on the gel formation of aqueous polyvinyl alcohol solution by cooling or chemically treating the solution.

This invention is based upon the findings that highly hydrous gels with excellent antithrombogenicity are produced by subjecting a cooled and solidified product obtained from an aqueous solution containing polyvinyl alcohol and asparaginase under specified conditions, without being molten, to a partial dehydration treatment, and the asparaginase embedded (entrapped) in the highly hydrous gel is capable of decomposing and eliminating the asparagine in blood flow without the formation of thrombi on the surface of the gel through which blood is passed.

DISCLOSURE OF THE INVENTION

This invention relates to a process for producing antithrombogenic immobilized enzyme preparations for the therapy of leukemia which comprises pouring an aqueous solution containing 6% by weight or more of a polyvinyl alcohol with a degree of hydrolysis of 97 mol. % or higher and a viscosity-average degree of polymerization of 1,800 or more together with L-asparaginase (asparaginase, L-asparagine amidohydrase), an asparagine-decomposing (hydrolyzing) enzyme into a vessel or a mold of an appropriate shape, subjecting the solution to cooling, solidifying and molding at a temperature lower than $-15°$ C. and partially dehydrating the molded mass without thawing to a dehydration ratio (ratio of weight decrease of the cooled, solidified and molded mass) of 5% by weight or more and, if desired, immersing the product in water to a water content of 45–92% by weight (on a wet weight basis).

BEST MODE TO CARRY OUT THE INVENTION

It is required that degree of hydrolysis of the polyvinyl alcohol used in the present invention is 97 mol. % or higher and preferably 98 mol. % or higher. Use of a polyvinyl alcohol with a degree of hydrolysis of 80–88 mol. %, especially 85 mol. % or lower will produce only a weak gel thereby not meeting the object of the invention.

Degree of polymerization of the polyvinyl alcohol used in the invention is required to be 1,800 or higher. With a degree of polymerization of 300–1,500 especially 1,100 or lower there will be formed only a viscous liquid or a weak gel. In the present invention, it is usually convenient to use commercially available products of a higher degree of polymerization (degree of polymerization of 1,800–2,600), although polyvinyl alcohols with a degree of polymerization, for example, of about 1,800–3,300 may be employed.

According to the process of the present invention, first, an aqueous solution at a polyvinyl alcohol concentration of 6% by weight or higher is prepared. The polyvinyl alcohol concentration may be, for example, 6–25% by weight. Although the concentration could be higher to about 90% by weight, viscosity of the aqueous solution at room temperature will reach 10,000 cP or higher, and the solution will undergo increase in viscosity or gel formation may take place. Therefore, use of the higher concentration will cause a little difficulty in handling.

Although this concentration could be lowered, for example, to 5% by weight or less, the dehydration time mentioned below will be delayed and the cost (power cost for dehydration) will be raised.

By the way, into this aqueous solution, preferably, as a buffer component for asparaginase, known tris(hydroxymethyl)aminomethane, phosphates or the like, for example, of pH 7–8.5 is added in the common manner.

According to the present invention, the aqueous polyvinyl alcohol solution prior to addition of an enzyme to the solution is sterilized, if required. The sterilization treatment may be at 100° C. for 5 min. to achieve the object in some instances. However, in the case where contamination with heat-resistant microorganisms exists, high pressure-steam sterilization, for example, at 120° C. for 15 min.–6 hours is applied. Whereas sterilization by ultraviolet irradiation may be employed, combined use with the afore-mentioned heat sterilization is preferable, because the former process is effective only on the surface irradiated. Any of these treatments will not result in deterioration of the materials to be employed in the invention, and there will be produced no problem at all in carrying out the invention.

The sterilized aqueous solution is then mixed with an enzyme to be immobilized. As the enzyme may usually be employed commercially available asparaginase of *Escherichia coli* B of the type EC-2 without further treatment. Besides, asparaginases of *Serratia marcescens, Proteus vulgaris, Bacterium cadaveris, Erwinia aroideae* and *Erwinia caratovora,* and furthermore of guinea pig serum may be employed. These asparaginases have already been reported to be therapeutically effective for leukemia (L. T. Mashburn, et al., Biochem. Biophys. Res. Commun., 12, 50 (1963), Arch. Biochem. Biophys., 105, 450 (1964), J. D. Broome, Nature, 191, 1114 (1961), J. Exp. Med., 118, 99, 121 (1963)). They can be useful for the side effect-free therapy by embedding in the hydrogels of the invention to inhibit the immunoreaction.

Commercially available asparaginase which is most common as an enzyme effective on leukemia is the one of *Escherichia coli* B of the type EC-2, which is available in freeze-dried powder or in 50% aqueous glycerin solution. Either of the two forms may be used in the present invention. Addition of the enzyme to an aqueous solution of a polyvinyl alcohol is preferably conducted at a temperature from 37° C. to room temperature in consideration of heat degeneration of the enzyme, although it may be carried out at a temperature of 70° C. or lower.

It is preferable to limit amount of the enzyme added to seven times the amount by weight of polyvinyl alcohol in the aqueous solution (expressed in terms of the weight of freeze-dried enzyme powders) in order to immobilize most of the enzyme. After the gel formation step as described later, about 85% by weight or more of the enzyme can be entrapped.

It has been confirmed by us that the polyvinyl alcohol in the present invention alone has a high enzyme-protecting activity and no additional enzyme-protecting agents such as glycerin, aspartic acid, aspartate, casein and the like are needed. Addition of these known protecting agents, however, may be made.

In the present invention, the aqueous solution containing both polyvinyl alcohol and asparaginase thus obtained is poured into a vessel of any shape or a mold of a desired shape and is subjected to cooling, solidifying and molding. Whereas it is preferred to use a mold of the shape for final use, a mold of any shape may be used with an intention of subsequent application of a transformation treatment such as cutting. Such is within the scope of the mold according to the invention.

As a cooling agent for the cooling, solidifying and molding may be employed, for example, a freezing agent such as sodium chloride-ice (23:77)(−21° C.) or calcium chloride-ice (30:70)(−55° C.), dry ice-methyl alcohol (−72° C.) or liquid nitrogen (−196° C.). Solidifying and molding are carried out after cooling to a temperature of −6° C. or lower. If cooling is insufficient, shape of the gel obtained after the dehydration described below will not be in exact conformity with the desired shape, namely, the shape of the vessel or the mold into which the aqueous solution of polyvinyl alcohol is poured. In addition, mechanical strength of the gel will be inferior. Although use of liquid helium will effect cooling to −269° C., it is preferable from the practical point of view to use a Freon freezer to achieve cooling, for example, to −35° C. or lower. Without the cooling, solidifying and molding, there will be formed only an enzyme-containing polyvinyl alcohol film as in the known processes which exerts no rigidity at all in water or a weak gel; there will not be produced an elastic, highly hydrous, water-resistant and antithrombogenic rubber-like enzyme preparation (hydrogel) according to the invention. In the cooling, solidifying and molding according to the invention, an aqueous solution of a polyvinyl alcohol is subjected to solidifying and molding in a mold of any shape, and subsequently, the upper cover or the lower cover, or both of the two, if any, are removed, and the molded article can be subjected to dehydration treatment while maintaining its shape. Therefore, the gel of the invention can be in any size and shape by the selection in consideration of convenience in the reaction of the immobilized enzyme and diffusion of the substrate and the reaction product. Preferred shape of the molded article can be produced by the use of a mold for forming Raschig ring, perforated plate, tellerette, intalox saddle, pall ring or the like which is used in chemical industry for the distillation tower, the gas absorption tower or the like, a mold for the column in which such filling material is placed, or a mold for the pipe used in extracorporeal blood circulation. A mold for the flat or curved plate with projection described in U.S. patent application No. 344,006 may also be employed. The immobilized enzyme preparations of the invention produced by the use of these molds are superior in contact with the substrate for the activity of the immobilized enzyme as well as in mass transfer. They are also superior in pressure loss of the extracorporeally circulated blood flow which is lower than that with simple granules, plates, films or microparticles. Of course, the granules, cuttings of the plates and other forms are covered by the present invention. Cooling rate in the cooling operation for the above-described cooling, solidifying and molding may be a slow cooling at a rate of about 0.1°–7° C./min. It may also be a rapid cooling at a rate of 7°–1,000° C./min.

After completing the cooling and solidifying of a mixed aqueous solution of a polyvinyl alcohol and an enzyme poured into a vessel or a mold as described above in the present invention, the molded article is subjected to dehydration under vacuum. When the cooled, solidified and molded mass is removed from the freezing room and promptly dehydrated by suction, the solidified and molded is not be thawed out without application of external cooling, because the material cooled as the moisture is removed (sublimed). Heating may be applied to such a degree that the cooled, solidified and molded article is not thawed out, by which the dehydration can be accelerated. As a matter of fact, there is no particular limitation to the temperature in the dehydration step provided that the cooled, solidified and molded article is not thawed out. Such temperature produces no noticeable influence upon the quality of the gel. Dehydration ratio in the dehydration step is 5% by weight or more to give a water content of the gel of 20–92%, preferably 60–90% by weight (on a wet weight basis). The water content may also be 20% or lower, and then can be increased to a water content of 50–90% by weight by immersing in water.

In the present invention, dehydration treatment (vacuum drying) is applied to the cooled, solidified and molded article to a certain extent regardless of the polyvinyl alcohol concentration. Dehydration ratio (ratio of weight decrease in the cooled, solidified and molded article) in this dehydration is 5% by weight or more, more preferably 15% by weight or more. In fact, since strength of the gel is remarkably increased and such properties as non-stickiness and resistance to water are much improved as dehydration proceeds, the partial dehydration treatment is essential in the present invention. However, the dehydration (drying) treatment may not be to such an extent as being sufficient for lyophilization of injectable pharmaceutical solutions or freeze-drying of aqueous foods such as coffee, milk, fruit juice and noodles, and the partial dehydration treatment as described above is sufficient to achieve the object of the invention. As described above, strength of the gel is remarkably increased as dehydration proceeds so that degree of the dehydration can be selected depending upon desired strength of the gel.

Since the partial dehydration treatment is essential and very significant in any embodiment of the present invention, there will no way be obtained those antithrombogenic hydrogels which are non-fluid, non-sticky and highly hydrous as well as have superior mechanical strength as described in the invention without the dehydration treatment. Moreover, if dehydration under reduced pressure of the cooled, solidified and molded article is carried out without maintaining the cooled and solidified state, that is, after thawing, the operation will be almost infeasible due to vigorous bubbling, and there will be formed only a turbid gel of poor elasticity even following a long duration of the dehydration.

Vacuum in the vacuum dehydration of the invention may be to any degree provided that water in the cooled and solidified article can be removed. A pressure at 10 mm.Hg or lower, preferably at 1 mm.Hg or lower and more preferably at 0.1 mm.Hg or lower is usually employed.

The product of the invention from the cooling, sodification, molding and partial dehydration is then allowed to stand, for example, at ordinary temperature to be thawed out thereby affording a gel rich in elasticity. Rate of the melting may be either a slow one at a rate of 1°–3° C./min. or a rapid one at a rate of 3°–1,000° C./min. Whereas melting point of a gel obtained by allowing an aqueous solution of a polyvinyl alcohol to stand (storing) at a temperature of about 0°–30° C. is around 15°–29° C., melting point of a gel according to the invention is as high as 60° C. or higher. Therefore, rapid thawing using warm water or air may be applied. However, as the gel of the invention is soluble in hot water and, at a temperature of 50° C. or higher, rapidly develops hard film on the surface, melting at a higher temperature should be avoided, and it is desirable to conduct the thawing at a temperature of 40°–50° C. or lower.

After the thawing operation, the gel can easily removed from the vessel or the support of the mold. It absorbs water in sterilized water or in sterilized physiological saline solution to a water content of 50–92% by weight (on a wet weight basis) in 1–6 hours, but still is a firm elastomer. The gel of the invention, which, as described above, contains water in a large proportion, exhibits a high elasticity. When strongly squeezed, it is temporarily transformed but promptly recovers the original shape with no deformation remaining. Also, when an adult person stands on a plate gel with a water content of 88% with one or both of the feet, the plate is temporarily transformed but promptly recovers the original shape with no deformation remaining. Heretofore, high water content and high mechanical strength have been considered to be a problem incompatible with each other in the development of medical polymers. On the contrary, the gel of the invention is satisfactory in both of the water content and the mechanical strength, and is a novel gel entirely different from prior-art films obtained by air drying an aqueous solution of a polyvinyl alcohol or prior-art water-soluble gels formed when an aqueous solution of a polyvinyl alcohol is simply stored at a temperature of 0°–30° C. or lower.

Even if pressure is applied to the gel of the invention, the water contained therein scarcely oozes out. For example, when a compressive stress of 4 kg/cm$^2$ is imposed on a gel with a water content of 90% by weight, the amount of water oozed out (flowed out) is only 1–2% of the total amount of water contained therein. As is apparent from the high water content of water firmly maintained as described above, apparent specific gravity of the gel is about as low as that of water. It barely sinks in water.

The gel of this invention has no stickiness. Even when about 10 g. of a gel which has been molded in plates (8 mm×8 mm×2 mm), in cylinders (3 mm in inner diameter, 6 mm in outer diameter and 6 mm in length) or in spheres (4 mm in diameter) is stirred in 50 ml. of sterilized water for 40 days, there is observed neither adhesion between particles nor deformation of the particles. When immersed in physiological saline solution for a year, there occurs no dissolution or no change in elasticity or strength. This is in striking contrast to noticeable deformation of devil's tongue jelly caused when immersed in tap water for several days. This is also in striking contrast to properties of the gel formed by simply cooling (freezing) an aqueous solution of a polyvinyl alcohol which exhibits a high stickiness, is merely a viscous fluid, or at best, jelly-, pudding- or agar-like and is so poor in resistance to water that it is readily dispersed or dissolved in water.

In the present invention, wet gels of desired form (particle, film, lump, plate, cylinder or any other form) can be produced by selecting any desired shape of the vessel or mold into which an aqueous solution of a polyvinyl alcohol is poured. The molding may be made in conformity with the shape of the final product, or the molded article thus obtained may be reformed into a different one, for example, by cutting or shaving.

Water content of the gel of the invention in which a large amount of water can be embedded is readily increased to 50–92% by weight by immersing the gel in water or physiological saline solution for 1–6 hours. Noticeably, water content of the gel obtained by subjecting a starting aqueous solution of polyvinyl alcohol in a concentration of 6–20% by weight to freezing, molding and partial dehydration according to the invention and subsequently immersing in water or physiological saline solution can be as high as 70–92% by weight. Therefore, the high water content gel of the invention, though being a rubber-like elastomer with such a high mechanical strength as mentioned above, often behaves just like water (or physiological saline solution) from the chemical or biochemical point of view and is almost non reactive with living tissue, being highly antithrombogenic when contacted with blood. As a matter of fact, whereas coagulation occurs when blood is contacted with glass, nylon, polystyrene, polyester, polyethylene, polyurethane foam, teflon, silicone or polyvinylpyrrolidone, it does not occur with a highly hydrous gel of the invention even under such conditions as forming thrombi with polyvinylpyrrolidone silicone, teflon or the like.

Poly(2-hydroxyethylmethacrylate) which has heretofore been watched as a hydrogel material for medical use usually contains water as low as 38–40% by weight and is inferior in mechanical strength (S. D. Bruck, J. Biochem. Mater. Res., 7, 389 (1973)). Although increase of the water content to about 60% by weight has been proposed, it is problematic that as the water content is increased, the mechanical strength becomes lower (J. D. Andrade (e.), "Hydrogels for Medical and Related Applications" p.23 (1976) ACS Symp. Ser.).

On the other hand, as there are easily produced highly hydrous gels usually having a water content of 70–92% by weight and even of 80–92% by weight in the present invention, and they are also superior in mechanical strength, they are valuable antithrombogenic materials being superior to any of prior art hydrophobic, hydrophilic materials and medical hydrogels.

Whereas the gel material of the invention is capable of easily permeating low molecular-weight substances such as asparagine (M.W. 132), aspartic acid (M.W. 133), ammonium hydroxide (M.W. 35), glucose (M.W. 180) and glycerin (M.W. 92), it is almost incapable of permeating enzymes with a molecular weight of about 100,000 and entirely incapable of permeating enzymes with a molecular weight of about 300,000 or more. Therefore, the asparaginase (M.W. 100,000–170,000) embedded in the gel of the invention will hardly be leaked out of the gel. Moreover, cells and macromolecular proteins in blood will not penetrate into the region of the embedded asparaginase so that antigen-antibody reactions caused by approach of the antibodies in the blood (lymphocytes, immunoglobulin (M.W.

160,000–890,000) to the asparaginase which is a foreign protein) within a distance of 0.1 nm or less is avoided.

In fact, some of the enzymes are liberated by immersing the formed gel of the invention in physiological saline solution. Then, however, continuation of the immersion (or washing) for an additional long period time would no longer cause liberation of the enzyme, and the gel can continuously (or repeatedly) used without possibility for the foreign protein to be liberated. Loss of the enzyme initially liberated by the immersion mentioned above is as low as about 10–15% of the amount of the enzyme employed prior to the gel formation in the present invention. Combined use of an enzyme liberation-preventive treatment may also be applied in the invention in order to avoid this loss of the enzyme. As a matter of fact, immersion treatment of an immobilized enzyme in an aqueous glutaraldehyde solution is often employed (T.M.S. Chang, Enzyme, 14, 95 (1972), G. Brown et al. Biotechnol. Bioeng., 15, 359 (1973)). When this known treatment is applied to the immobilized enzyme preparations of the invention, the aforementioned loss from liberation of the enzyme is greatly reduced to a level of 1–2% of the original amount of the enzyme. The immersion treatment in an aqueous glutaraldehyde solution is favorably used for the gel of the invention because of simultaneous sterilization of the immobilized enzyme preparation due to sterilizing action of the aqueous solution.

The hydrogels of the invention is a material which is very lowly harmful to living tissue, because they are not reactive when directly contacted. For example, a hydrogel ($1 \times 1 \times 1$ cm) was implanted subcutaneously in the rabbit on the back for a period of 1–3 months and subjected to histological examination. The gel was tightly adhered to and encapsuled by living tissues. The living tissues were incised to find that the whole gel was surrounded uniformly by thin film, which was easily stripped off with a knife. There was observed no cellular infiltration in the film and other living tissues, thereby indicating no inflammation reaction. Such good biocompatibility of the hydrogel of the invention enables residence of the immobilized enzyme preparation of the invention with asparaginase embedded in the abdominal cavity in place of the well-known therapy of intraperitoneal free asparaginase administration (J. G. Kidd, J. Exp. Med., 98, 565, 582 (1953)).

As described above, the hydrogels of the invention are highly hydrous gels having high antithrombogenic activities, and therefore can also be used as an immobilized enzyme preparation constructing an extracoporeal circuit of blood. It is however admitted that behaviors perfectly identical with those of water of physiological saline solution cannot be guaranteed with the highly antithrombogenic hydrogels of the invention however high the hydration is. Although it is reasonable to consider that increase in water content of the material will contribute to increase in antithrombogenic activity, the water content cannot be increased without limitation so far as medical material (structures) are concerned (in order to assure a mechanical strength). Water content of the hydrogel of the invention can far exceed the upper limit of water content in hydrogels of polyvinyl alcohol-gluraraldehyde or poly(2-hydroxyethylmethacrylate)(60–80%)(E. W. Merrill et al., ACS Polymer Preprint, 13, 513 (1972)), but water content exceeding 92% by weight will result in decrease in mechanical strength of the gel.

With the object of maintaining satisfactory antithrombogenicity for a long period of time while fixing water content of the gel of the invention within a range between 45 and 92% by weight, an antithrombogenic agent (anticoagulant) may be embedded in the gels of the invention.

As the antithrombogenic agent are effective heparins (heparinic acid, sodium heparinate, potassium heparinate, calcium heparinate and magnesium heparinate). In order to maintain the antithrombogenicity for a long period of time more firmly by embedding the aforementioned antithrombogenic agent in the highly hydrous gel of the invention powders, an aqueous solution or a suspension of a heparin is added to the starting aqueous solution according to the invention, namely, an aqueous solution containing a polyvinyl alcohol and an enzyme and the mixture is blended. Concentration of the heparin in this process may be 10% by weight or lower. Although a larger amount of heparin may of course be added to the aqueous solution to prepare a suspension, it is usually unnecessary to add such larger amount of heparin, as the heparin embedded in the hydrogel of the invention will not be effluted within a short period of time and will remain embedded while being sustainedly released.

In the present invention, above-mentioned cooling, solidification, molding and partial dehydration treatments of the aqueous solution of polyvinyl alcohol, enzyme and heparin enable uniform dispersion and embedding in the gel of 99% or more of the heparin from the aqueous solution. Form of the gel can be stabilized in wet gel with a water content of 50–92% by weight in nearly equilibrated hydration by known gluraraldehyde treatment and subsequent from one-to six-hour immersion in sterilized water or physiological saline solution. A small amount of the heparin is effluted out of the hydrogel during the immersion operation, but the loss is usually as low as about 0.5–1% of the total amount embedded with no influence upon antithrombogenicity of the hydrogel of the invention. For example, sodium heparinate was dissolved at a concentration of 3% by weight in an aqueous solution of polyvinyl alcohol. The mixture was subjected to the treatments according to the invention to obtain 5 g. of a gel (total surface area 50 cm$^2$, embedded heparin 4800 units (30 mg.)/g.). The gel was immersed in 5 ml. of physiological saline solution for 6 hours to observe an effluent (loss) of the heparin of about 0.6%. When subsequently contacted with blood flow in the body for 28 days or longer, there remained heparin on the surface of the hydrogel. As compared with heparin embedded in an aldehyde-bridged gel of a polyvinyl alcohol, which is entirely effluted in 5–8 hours usually or in about 5 days at longest, heparin embedded according to the present invention shows a unique sustained-release effect and evidently is very advantageous in medical materials. The gel of the invention is easily obtained in any shape. For example, a hydrogel pipe or an embedded heparin-containing pipe 2–6 mm in diameter can be produced and used as extracorporeal circulation of blood. Currently available artificial blood vessels of polyester or teflon is highly thrombogenic and has difficulties as a replacement for fine arteries 5 mm or less in diameter. Besides, it is not applicable to venous region where blood flow is slow. On the other hand, the hydrogel pipe or embedded heparin-containing hydrogel pipe, even for the flow 2–5 mm in diameter, does not cause thrombus over a period of at shortest 4 weeks. In the course of this circulation the hydrogel pipe or embedded heparin-containing hydrogel pipe is covered with thinly adhered living tissues (protein) throughout the surface thus indicating satisfactory biocompatibility.

There is no need in the present invention to worry about association of harmful substances with the hydrogel (or embedded heparin-containing hydrogel) of the invention so far as washing and removed of the unreacted glutaraldehyde after used for the known aftertreatment. Polyurethane-dimethylsiloxane which is a typical antithrombogenic material of the prior art is always encountered with possibility for tetrahydrofuran, dioxane, acetic acid, etc. to be accompanied by, and moreover, so readily adsorbs dusts in a sterilized room that it should be handled in a special clean room different from the conventional operation room. On the other hand, it is very easy to handle the hydrogel and embedded heparin-containing hydrogel of the invention.

Although the mechanism by which those antithrombogenic highly hydrous gels which are entirely distinguishable in high mechanical strength and elasticity from known polyvinyl alcohol gels are produced by cooling, sodification, molding and partial dehydration of an aqueous solution of a polyvinyl alcohol is not clear, it is believed that a large number of intramolecular and intermolecular entaglements are formed during the cooling, solidification, molding and subsequent partial dehydration, and especially during the partial dehydration to enhance the mechanical strength and the elasticity.

Anyhow, such antithrombogenic immobilized enzyme preparations and the process for preparing the same by cooling, solidification and partial dehydration of polyvinyl alcohol are novel ones discovered by us.

The immobilized enzyme preparations according to the present invention show high remission to lymphocytic leukemia, myelocytic leukemia, especially acute lymphatic leukemia, and can also be applied to various leukemias for which known free asparaginases have been recognized to be effective, such as acute myeloid leukemia and chorioepithelioma malignum (or diseases similar to leukemias, solid tumor such as melanoma).

In the immobilized enzyme preparations according to the present invention, as mentioned above, the immunoreaction is avoided and therefore they can be used for introducing, further maintaining and improving remission without concerning the side effect.

The asparagine-decomposing activity of the immobilized enzyme preparations according to the present invention is reduced to 80–90% of the initial value after continuous use for about a week and to a half after continuous use for about a month. In some cases depending upon recovery of the symptoms, therefore, renewal of the immobilized enzyme preparation is needed. However, as compared with the prior-art process in which a high dose (for example, 10,000 units per 50 kg. bodyweight, ca, 75 mg./day) of the expensive enzyme is repeatedly drip-infused (disposed) daily or every two days for a long period of 4–28 days, the regimen according to the invention by which the immobilized enzyme preparation can remain in contact with blood flow for a long period of time is superior from the operational and economic points of view.

The enzyme preparations are relatively easily handled, being stable for about 6 months on the conditions that they are stored at 0°–10° C. after manufactured with 10% or less of activity reduction observed.

The invention will be described below with reference to examples.

EXAMPLE 1

In 201 g. of an aqueous solution of tris(hydroxymethyl)aminomethane-hydrochloric acid (50 mM-0.2 mM) at pH 8 was added 32.8 g. of a commercially available powdery polyvinyl alcohol (degree of hydrolysis 99.4 mol. %, viscosity-average degree of polymerization 2,600, viscosity of the 4% aqueous solution at 20° C. 66 cP)(water content 8.5% by weight) to a 13% by weight aqueous solution. With 25 g. of the aqueous solution was blended at room temperature 6.9 g. of a L-asparaginase solution (commercial product, 50% aqueous glycerin solution, 290 units/ml.) to give an aqueous solution containing 10% by weight of the polyvinyl alcohol, 10% by weight of glycerin (the solvent for the commercially available enzyme solution) and 0.04% by weight of the enzyme (pH 8).

Into a mold for the pipe molding 1 mm in inner diameter, 3 mm in outer diameter and 1 m in length was poured 6.3 ml. of the aqueous polyvinyl alcohol-asparaginase solution, followed by cooling at −40° C. for 4 hours. Then, the upper cover of the mold was removed, and the cooled, solidified and molded mass was subjected to vacuum dehydration for 6 hours without thawing. The vacuum was put off and the molded article (gel in the form of a pipe) was taken out. After thawing, there was obtained a pipe weighing 5.3 g. (ratio of dehydration 15% by weight, liquid content 88% by weight), 1 mm in inner diameter and 2.7 mm in outer diameter. The pipe was immersed in 1% aqueous solution of glutaraldehyde at room temperature for 15 min. and then at 5° C. overnight. Washing was repeated 10 times each with 30 ml. of an aqueous solution of tris(hydroxymethyl)aminomethanehydrochloric acid (47 mM-0.3 mM) at pH 7.5 containing 0.9% by weight of sodium chloride (sterilized) to obtain 5.7 g. of a hydrogel pipe (liquid content 89% by weight). It is noted that a large amount of the aldehyde and a trace of protein were detected in the washings at the initial stage but none of them was detected in the washing after completion of the washing operation.

In a polyethylene bag sterilized with gaseous propylene oxide (at room temperature for 10 hours) and subsequently degassed under vacuum was placed the above-prepared hydrogel pipe, and the bag was tightly closed.

Between the femoral artery of the right posterior limb and an extracorporeal shunt of the femoral vein of the left posterior limb of a beagle dog weighing 6 kg. was connected the embedded asparaginase-containing pipe from the above-mentioned polyethylene bag. The dog was allowed to be under natural blood flow. Asparagine concentration in the arterial blood flow was reduced from 36 mM (475 ppm) to 0.5 mM (6.6 ppm) after 4 hours, being no longer detected (1 ppm or below) after 5 hours.

EXAMPLE 2

A piece of an embedded asparaginase-containing pipe obtained by the same procedures as in Example 1 (7 cm in length) was loaded with a tensile strength of 5 kg/cm$^2$. It was found that the pipe was not broken.

When a piece of the same pipe (4 cm in length, 0.25 g.) was incised to prepare a thin plate which was loaded with 4 kg/cm$^2$. Weight decrease due to exudation of water was only 2 mg.

A piece of the same pipe (9 mm in length) was inserted into the cervical vein of a dog (body-weight 7 kg.) by the following procedures. The cervical vein was aseptically exposed under intravenous pentobarbital anesthesia and intubated regulation of respiration. After the adventitia was stripped off, a longitudinal incision was made in a length of 5 mm. Central and peripheral ends of the incision were tied respectively with a thread to block blood flow temporarily. Immediately after the operation, inner cavity of the vein was washed with sterilized physiological saline solution, and the piece of the pipe (ring) mentioned above was inserted on the peripheral side while cautiously avoiding injury of the intima of the blood vessel. The ring was then pulled toward the central side to unite the incision line and the center of the ring. The incision line was closed with a catgut 0.18 mm in diameter which had been sterilized with ethylene oxide. Then, while resuming blood flow, the center of the inserted ring was ligated. After 2 weeks, the same region as above was reopened to observe a thin film throughout the surface of the ring. There was observed no thrombogenesis.

Comparative runs done respectively with a silicone rubber ring and a teflon ring in dogs weighing 7–15 kg. revealed that a marked thrombogenesis was observed in as short as 2 weeks, with the blood vessel almost obstructed, thereby indicating superiority of the embedded enzyme-containing hydrogel of the invention in antithrombogenicity.

COMPARATIVE EXAMPLE 1

Into a square vessel 6×6 cm in size on the bottom surface was poured 30 g. of the same aqueous solution of polyvinyl alcohol and asparaginase as in Example 1, which was allowed to stand at ordinary temperature for 2 days. There was obtained a colorless clear soft film. When the film was immersed in tap water for 6 hours, it was partly dissolved in water and the residual film was sticky. There was not produced the rubber-like gel as in Example 1 at all.

This indicates that drying alone of an aqueous solution containing polyvinyl alcohol and enzyme does not produce a rubber-like highly hydrous enzyme-containing gel.

COMPARATIVE EXAMPLE 2

The same procedures as in Example 1 were repeated using a commercially available polyvinyl alcohol having a degree of hydrolysis of 78.5 mol. %, a viscosity-average degree of polymerization of 1,800 and a viscosity of 4% aqueous solution (20° C.) of 36 cP in place of the polyvinyl alcohol used therein. There was obtained 5.7 g. of a cooled, solidified, molded and dehydrated product (degree of dehydration 10% by weight), which, after molten, was softened at 5° C., thereby a small amount of the gel layer and a large amount of the thick aqueous solution of polyvinyl alcohol being observed.

This indicates that use of a polyvinyl alcohol having a low degree of hydrolysis does not produce a water-resistanct gel with the enzyme embedded as in the present invention.

COMPARATIVE EXAMPLE 3

The same procedures as in Example 1 were repeated using a commercially available polyvinyl alcohol having a degree of hydrolysis of 99.2 mol. %, a viscosity-average degree of polymerization of 500 and a viscosity of 4% aqueous solution (20° C.) of 5.6 cP in place of the polyvinyl alcohol used therein. There was obtained 5.7 g. of an agar-like fragile gel (degree of dehydration 10% by weight).

This indicates that use of a polyvinyl alcohol having a low degree of polymerization does not produce a rubber-like enzyme-containing gel having a high mechanical strength as in the present invention.

COMPARATIVE EXAMPLE 4

The same aqueous polyvinyl alcohol-enzyme solution as in Example 1 was cooled, solidified and molded at −40° C. and then allowed to stand at ordinary temperature for 3 hours. There was formed a weak sticky gel (6.3 g.), which had a poor elasticity and a so low tensile strength that is was broken with a load as small as 0.3 kg/cm$^2$. When 1 g. of the gel was immersed in 3 ml. of water, it was deformed in about 20 hours to give a turbid aqueous layer which indicated considerable dissolution of the polyvinyl alcohol.

As described above, cooling, sodifying and molding of an aqueous solution of polyvinyl alcohol and enzyme would produce, after molten, only a sticky gel having a low mechanical strength and a low water-resistance. There will not be formed a water-resistance embedded enzyme-containing gel with a high mechanical strength unless partial dehydration is applied without thawing to the cooled, solidified and molded product according to the present invention.

The same hydrogel pipe as obtained in Example 1 (1 m in length) was cut in 4-cm portions. A suture test was conducted by anastomosing the pieces with a silk knitted thread (JIS No. 1, 0.1 mm in diameter, sterilized at 120° C. for 30 min.) which had been subjected to a dissolution treatment with sericin, a catgut (intestine wire, 0.18 mm in diameter. Sterilized with ethylene oxide), a Dexon thread (polyglycolic acid, 0.18 mm in diameter, sterilized at 120° C. for 30 min.) and a taper cut needle respectively at a thread distance of 1.5 mm.

With any of the sutures employed, the enzyme-containing hydrogel pipe of the invention was easily sutured and was encountered with no breakage at all at the site of suture, thereby suggesting that the pipe is strong enough to be sutured with blood vessels in the living tissue.

An antithrombogenicity test of the hydrogel pipe was also done in the same way as in Example 2 to indicate that no thrombogenesis was observed.

EXAMPLE 3

In 914 g. of Tris buffer solution at pH 7.5 was dissolved 86 g. of a commercially available polyvinyl alcohol powders (a degree of hydrolysis of 97 mol. %, a viscosity-average degree of polymerization of 1,800 and a viscosity of 4% aqueous solution (20° C.) of 28 cP)(water content 7% by weight) to a 8.0% by weight solution.

To 41 g. of the aqueous solution sterilized in the same way as in Example 1 was added with stirring at 33° C. 82 mg. of L-asparaginase (lyophylized powder, 250 units/mg.). Into a square polyethylene vessel 7×7 cm in size on the bottom surface was poured 40 g. of the above-prepared aqueous solution, which was cooled at −50° C. for 6 hours. It was then subjected to vacuum dehydration for 6 hours without melting. The vacuum was then put off, and the molded article (ca. 7 mm in thickness) was removed and molten. There was obtained 33 g. of a white opaque gel (degree of dehydration 18% by weight, water content 90% by weight).

A piece 20 mm×13 mm×5 mm in volume was cut from the hydrogel and used as a test material to be implanted in the body.

The skin of a rabbit (bodyweight 2.5 kg.) on the back was shaved and applied with 0.5% ethyl alcohol solution of chlorohexidine. The shaved area was sterilized with 70% ethyl alcohol and then incised in a length of ca. 1.5 cm. The above test material was implanted in the area, and the skin was sutured. Position of the implanted test material was adjusted so as not to be overlapoed with the incision line. After 24 hours, rubefaction and slight oncoides were observed, and the implanted test material was moved within the detached region of the subcutaneous tissue. After 3 days, the oncoides and the rubefaction disappeared, and the sutures were removed after 6 days. After 8 days, the test material was fixed and did not move by palpation. Later for 1 month, no changes were observed on the implanted region, and no systemic symptoms were also observed. After 30 days, the test material was excised together with the subcutaneous tissue. The material was mantled with the capsule cell, which were not adhered but were closed attached. The capsule was treated (fixed) with 10% formalin and embedded in paraffin, followed by hematoxylineosine double staining and van Gieson staining. There were observed a small number of pseudoacidocyte and round cell but very slight cellular infiltration and almost no inflammation reaction.

On the other hand, strong foreign body reaction was observed around the catgut used as the suture after removal of the sutures. For comparison's sake, a sponge 20 mm×13 mm×5 mm in volume was subcutaneously implanted in a rabbit on the back in the same way as above. Disappearance of rubefaction and the oncoides took 14 days. Excision after 1 month revealed that volume of the sponge was decreased by about 10%, and strong infiltration and a number of foreign body giant cell was observed in the circumferential portion of the sponge. In a comparative test with methylmethacrylate resin, it took a week for the rubefaction and oncoides to disappear and there was observed marked infiltration of pseudoacidocyte. It was thus found that the hydrogel of the invention was far superior in biocompatibility.

EXAMPLE 4

A test material to be implanted in the body was prepared by subjecting a piece of the hydrogel obtained in Example 3, 13 mm×13 mm×1.5 mm in volume to immersion in 2% by weight aqueous solution of glutaraldehyde at room temperature for 15 min. and at 6° C. for 8 hours and washing with 10 10-ml. portions of Tris buffer solution.

Longitudinal incision was made at medial knee joint of rabbit (bodyweight 2.5 kg.) in a length of 3 cm. Longitudinal incision was made at medial musclus quadriceps femoris, and the pastella was exteriorly dislocated. While bending the knee joint, adipose tissue of anterior surface was resected, and the crossed ligamentum was cut. Then, the joint capsules other than the posterior joint capsule and the meniscus were resected. Subsequently, the femoral articular cartilage was resected. The above test material was inserted on the femur articular surface in place of the cartilage, and fixed. Knee joint was flexed at an angle of 150°, then plastar bandage was applied from upper part of the femur through the foot. It was removed 3 weeks later, there were observed at the joint slight swelling, but neither rubefaction nor local fever, good primary coaptation and no exudate. The knee joint had a flexor of about 120° and protected limping gait was observed. Knee joint was moved by force in a range between 150 and 90°. Specimens were fixed with formalin, embedded in paraffin, stained with hematoxylin and eosin, subjected to Mallory's staining and microscopically examined. Articular surface of femur was encapsuled with connective tissues and neither reactive ossein hyperplasia, nor inflammation of medullary space due to the implanted test material.

A comparative test was carried out with a methylmetharylate resin 1.5 mm in thickness in the same manner as above. Findings after 3 weeks were as follows: There were observed swelling at the joint, and in addition, local fever and palpation of undulating movement on the upper part of patella. The knee joint was only slightly movable by force but not spontaneously movable. There were observed inflammatory cellular infiltration and fibrous cicatrization. These findings indicated that the enzyme-containing hydrogel according to the invention was superior in biocompatibility.

EXAMPLE 5

Eight pieces each 13 mm×13 mm×1.5 mm in volume from the hydrogel produced in Example 4 were subjected in the same way as in that example to glutaraldehyde treatment and washing. The above 8 pieces were intraperitoneally implanted in mice with blebs formed by subcutaneous injection of 600,000 cells of 6C3HED lymphosarcoma (J. G. Kidd, J. Exp. Med., 98, 565, 582 (1953), J. D. Broome, J. Exp. Med., 118, 99, 121 (1963)) at the shaved area of the foot groin just beneath the costal margins. On the 30th day after the implantation no sarcoma was visually observed and palpation indicated no abnormalities. Asparagine concentration was reduced from an initial value of 30 mM (400 ppm) to 0.2 mM (3 ppm) on the second day, which remained unchanged throughout the experiment.

COMPARATIVE EXAMPLE 5

The mice subcutaneously administered with the same lymphosarcoma as in Example 5 were subjected to intraperitoneal injection of 2 ml. of physiological saline solution alone. Papular tumors 2–3 mm in diameter were observed on the skin at the site of subcutaneous injection after 7 days. The result evidently indicates that the asparaginase employed in example given above has a tumor-inhibitive effect.

COMPARATIVE EXAMPLE 6

When 2 ml. of physiological saline solution containing asparaginase powders dissolved therein (enzyme 2 mg./ml., 500 units/ml. was intraperitoneally injected in place of the physiological saline solution used in Comparative Example 5, lymphosarcomas (3mm in diameter) were developed after 11 days.

As already pointed out, administration of free asparaginase produces effects of a short duration in general. The foreign protein is considered to disappear in a relatively short period of time by the attack of proteinases in the body. Accordingly, proposed use of asparaginase is repeated administrations every 6 hours or every 2 days usually at a high dose (L. T. Mashburn et al., Biochem. Biophys. Res. Commun., 12, 50 (1963), R. H. Adamson et al., Cancer Chemther. Rep., (1)52, 617 (1968)), which often produce severe side-effects. On the contrary, durable effects of the immobilized enzyme preparation of the invention are evidently demonstrated in Example 5.

EXAMPLE 6

A beagle strain dog (female, 5 years old 6 kg.) having edema 30 mm×30 mm in size in the submandibular region and symptoms such as anorexia, tonsillar enlargement, and enlargement and inflammation of the soft palate was diagnosed lymphosarcoma by biopsy.

Eight pieces of the immobilized asparaginase-containing hydrogel obtained in the same way as in Example 5 were intraperitoneally implanted in the dog. The dog recovered appetite on the next day. The lymph nodes were softened and reduced to 3 mm×3 mm after 2 days. Degenerating lymphoblasts were observed by microscopic examination. Further 2 days later, the lymph nodes disappeared. No abnormalities were observed after 50 days.

EXAMPLE 7

Lymph nodes of a 6-year dog (male, 2.94 kg.) with anorexia and in lethargy were diagnosed lymphosarcoma by biopsy.

Eight pieces of the immobilized asparaginase-containing hydrogel obtained in the same was as in Example 5 were intraperitoneally implanted in the dog. After 2 days, the dog recovered appetite, and softening of the lymph nodes was confirmed by palpation.

Further 2 days later, the lymph nodes were reduced to 2 mm×2 mm, and the dog became alert and vivid.

Further 2 days later, the lymph nodes almost disappeared, and there were observed in the cortex by biopsy many necrosis and islands of undifferentiated lymphoblasts in mitosis. Further 3 days later, the dog was recovered to detection of no lymphoblasts.

EXAMPLE 8

A shepherd dog 5 years old (3.5 kg.) having superficial lymph nodes 40 mm×30 mm in size at the politeal area and symptoms such as recurrent vomiting, lymphoid enopathy, splenomegaly, tonsillar enlargement and edema of scrotum was administered with atropine to inhibit vomiting and then implanted intraperitoneally with 8 pieces of the immobilized asparaginase-containing hydrogel. After 3 days, the dog recovered appetite and was alert. The lymph nodes were reduced to 2 mm×2 mm. The splenomegaly and the tonsillar enlargement were also reduced markedly. The edema of scrotum disappeared. There were no abnormalities in serum uric acid, serum urea nitrogen, erythrocyte count and leukocyte count. Further 3 days later, the lymph nodes also disappeared.

I claim:

1. A process for producing immobilized L-asparaginase preparations for the therapy of leukemia which comprises pouring an aqueous solution containing 6% by weight or more of a polyvinyl alcohol with a degree of hydrolysis of 97 mol. % or higher and a degree of polymerization of 1,800 or more and an antileukemic asparaginase into a vessel of a desired shape and subjecting the solution to cooling and solidification at a temperature lower then $-15°$ C., and then partially dehydrating the resulting solidified mass without thawing to a dehydration ratio of 5% by weight or more to obtain a desired gel.

2. The process according to claim 1 wherein heparin is added to the aqueous solution.

3. The process according to claim 1 or 2 wherein concentration of the polyvinyl alcohol in the aqueous solution is from 6 to 25% by weight.

4. The process according to any one of claims 1-3 wherein the cooling, solidification and molding temperature is $-35°$ C. or below.

5. The process according to any one of claim 1-4 wherein dehydration ratio in the partial dehydration step is 15% by weight or more.

6. The process according to any one of claims 1-5 wherein the partial dehydration is conducted by vacuum dehydration.

7. The process according to any one of the claims 1-6 wherein the water content of the obtained gel is increased by immersing said gel in water to give a water content of 45 to 92% by weight.

* * * * *